United States Patent
Schmitt

(12) 
(10) Patent No.: US 6,733,176 B2
(45) Date of Patent: May 11, 2004

(54) X-RAY EXAMINATION DEVICE FOR CEILING MOUNTING

(75) Inventor: Thomas Schmitt, Forchheim (DE)

(73) Assignee: Siemens Aktiengesellschaft, Münich (DE)

( * ) Notice: Subject to any disclaimer, the term of this patent is extended or adjusted under 35 U.S.C. 154(b) by 67 days.

(21) Appl. No.: 10/232,192

(22) Filed: Aug. 30, 2002

(65) Prior Publication Data

US 2003/0068008 A1 Apr. 10, 2003

(30) Foreign Application Priority Data

Aug. 31, 2001 (DE) .......................................... 101 42 441

(51) Int. Cl.⁷ ................................................. H05G 1/02
(52) U.S. Cl. ....................................... 378/196; 378/197
(58) Field of Search ................................ 378/193–197

(56) References Cited

U.S. PATENT DOCUMENTS 4,501,011 A * 2/1985 Hauck et al. ............... 378/196

FOREIGN PATENT DOCUMENTS

| DE | 87 06 822 | 10/1988 |
|---|---|---|
| DE | 196 11 705 | 10/1997 |
| EP | 0 877 538 | 11/1998 |

* cited by examiner

Primary Examiner—Craig E. Church
(74) Attorney, Agent, or Firm—Schiff Hardin LLP

(57) ABSTRACT

An X-ray examination device for mounting at a ceiling of an examination room has a support mechanism for a patient to be examined, a first adjustment device attachable to the ceiling for holding and moving an X-ray radiator, and a second adjustment device attachable to the ceiling for holding and moving a radiation receiver. The adjustment devices are arranged and fashioned such that the X-ray radiator as well as the radiation receiver can be brought from one side with respect to the middle longitudinal axis of the support mechanism onto the opposite side. The adjustment devices each have guide rails at which transverse carriers are movable. The X-ray examination device allows an especially large number of examination techniques and transillumination perspectives.

13 Claims, 6 Drawing Sheets

X-RAY EXAMINATION DEVICE FOR CEILING MOUNTING

BACKGROUND OF THE INVENTION

1. Field of the Invention

The present invention is directed to an X-ray examination device for mounting at a ceiling of an examination room.

2. Description of the Prior Art

An X-ray examination device is disclosed in German OS 196 11 705 having a support mechanism for a patient to be examined, an X-ray radiator, a radiation receiver for detecting X-rays emitted by the X-ray radiator, a first adjustment device attachable to the ceiling for holding and moving the X-ray radiator, and a second adjustment device attachable to the ceiling for holding and moving the radiation receiver.

SUMMARY OF THE INVENTION

An object of the present invention is to provide an X-ray examination device of the above type wherein the user-friendliness is improved so that a greater number of examination techniques or examination modes is possible.

This object is achieved in an X-ray examination device of the above type wherein the adjustment devices are arranged and fashioned such that both the X-ray radiator and the radiation receiver can be brought from one side of the middle longitudinal axis of the support mechanism to the opposite side.

The invention is based on the perception that an X-ray exposure with a known X-ray examination device of the initially described type can be made only proceeding from one side of the patient, since the radiation receiver and the X-ray radiator cannot interchange their positions with respect to the support mechanism. One consequence thereof, for example, is that the left hip as well as the right hip of the patient can be registered proceeding only from the left. Particularly when registering the right hip, this means that some details in the X-ray image or transillumination image can be seen only poorly. Another consequence is that the operators or physicians must familiarize themselves with an extremely large number of transillumination images, for example in order to compare these to reference images in textbooks or exposure-assisting booklets.

In the inventive X-ray examination device, a switch can be advantageously made from right operation to left operation. For example, the left hip of the patient can be transilluminated from the left and the right hip of the patient can be transilluminated from the right. An especially large number of transillumination perspectives are thus possible.

In a preferred development, the first adjustment device has a first guide rail and the second adjustment device has a second guide rail that are perpendicularly arranged with respect to the middle longitudinal axis of the support mechanism.

It is especially advantageous for a first transverse carrier to be movably attached to the first guide rail and a second transverse carrier to be movably attached to the second guide rail. The X-ray radiator is attached to the first transverse carrier and the radiation detector is attached to the second transverse carrier. The attachment is such that the X-radiator and the radiation receiver are movable perpendicularly to the first guide rail or, respectively, perpendicular to the second guide rail.

As a result of the combination of a separate guide rail with a separate transverse carrier, the X-radiator as well as the radiation receiver is laterally or horizontally movable—each independently of the other.

The guide rails preferably are fashioned as ceiling rails and allow movability perpendicularly to the patient axis (y-direction). The transverse carriers allow adjustability along the patient axis (displaceability in the x-direction).

As used herein, "guide rail" means any guide element suitable for a defined motion. The transverse carriers, for example, are movably mounted at the respective guide rail and are thus horizontally movable perpendicularly to the patient axis. In this case, the transverse carriers could also be referred to as carriages or trucks or cross-trucks, i.e. components that are displaceable at the guide rails and that allow a transverse motion relative to the guide rails. For realizing motion transverse relative to the respective guide rail, a carriage, a truck or a column can in turn be movably mounted in the respective transverse carrier.

In order to allow the examination of the entire patient body without repositioning the patient, it is expedient that the length of the first transverse carrier and/or the length of the second transverse carrier is greater than 1.5 m.

According to a preferred development the transverse carriers, as seen in a vertical longitudinal side view, are arranged above one another at least in sections. The X-ray radiator and the radiation receiver can be suitably aligned relative to one another for an X-ray exposure in this overlapping section. The overlapping section, in particular, is greater than the width of the truck, preferably greater than 1.5 m.

According to another preferred development, as seen in a vertical, longitudinal side view, one of the transverse carriers projects beyond the other transverse carrier. It is possible in a simple and especially advantageous way to accomplish a side change of either the X-ray radiator or of the X-ray receiver from one side of the bearing mechanism onto the other side in the projecting part of the appertaining transverse carrier.

It is also especially advantageous for this purpose for the transverse carrier to be attached such at different heights that the transverse carriers can be moved past one another given movement directed opposite one another.

In another preferred development, at least one of the transverse carriers has the majority of its length projecting laterally beyond the appertaining guide rail, which projects at only one side of this guide rail as a boom. As a result, it is assured that X-ray images can be registered over the full length of the patient and it is also assured that the two transverse carriers or cross-trucks can travel past one another in a simple way.

The boom preferably is supported by a floor support, preferably at its end facing away from the guide rail. The stability of the boom-like transverse carrier thus is increased.

For this purpose, the floor support can carry a third guide rail for guiding the boom. For example, the third guide rail can be attached to the upper end of the floor support and can proceed, for example, parallel to the first guide rail and/or to the second guide rail.

According to another preferred development, as seen in a longitudinal view, the other transverse carrier projects beyond the boom-like transverse carrier, and preferably also beyond the floor support that the X-radiator or radiation receiver carried by the other transverse carrier, so that it can travel past at that side of the floor support facing away from the boom-like transverse carrier. In other words: for changing sides, the X-ray radiator or the radiation receiver moves past the other transverse carrier behind the floor support and onto the other side of the bearing mechanism.

In a preferred embodiment, the X-ray examination device have a louver wall device. A louver wall device is described, for example, in a data sheet of Siemens AG having order number "A910010M1210-G482-05" and having the title "Vertix 2/Vertix 2E". In conjunction with the inventive X-ray examination device, it is especially advantageous to employ the louver wall device a floor support. For example, a carrying structure of the louver wall device is employed for the floor-side support of at least one of the adjustment devices.

According to another preferred embodiment, a control device is present with which drive means for moving the X-radiator and the radiation receiver are controllable such that the side change of the X-radiator and/or of the radiation receiver can be automatically implemented. This is comfortable for the operating personnel and collisions can be avoided under program control.

DESCRIPTION OF THE PREFERRED EMBODIMENTS

Figure 1:
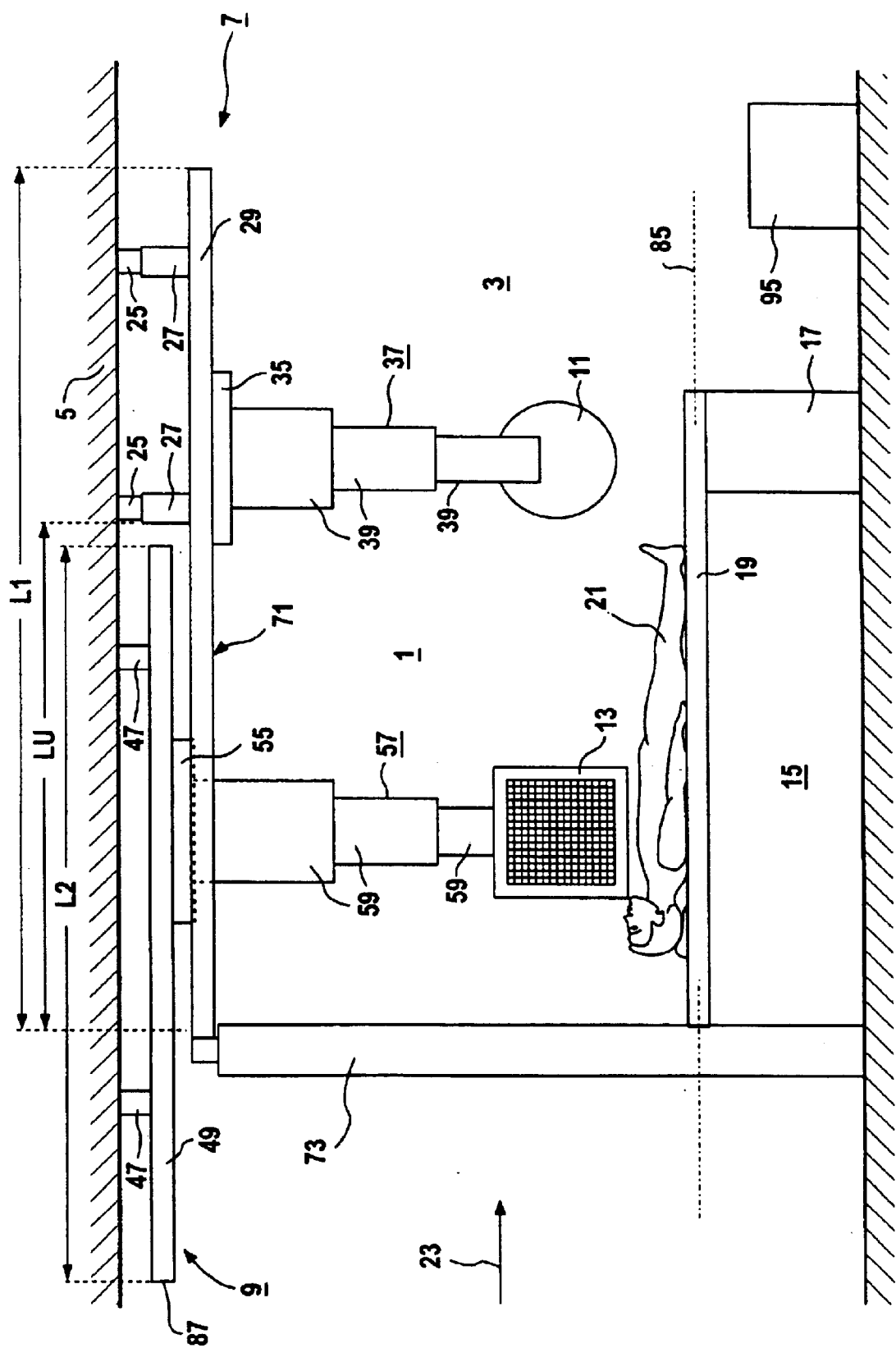
FIG. 1 shows a first exemplary embodiment of an X-ray examination device of the invention in a longitudinal side view.

FIG. 1 shows an X-ray examination device 1 of the invention that is installed in an examination room 3 with a ceiling 5. The X-ray examination device 1 has adjustment devices 7, 9 for holding and moving an X-ray tube or an X-radiator 11 and a radiation receiver 13 respectively allocated thereto. The X-ray examination device 1 also has a support mechanism 15 with a height-adjustable base 17 that carries a patient bed 19 for placement of a patient 21.

Figure 2:
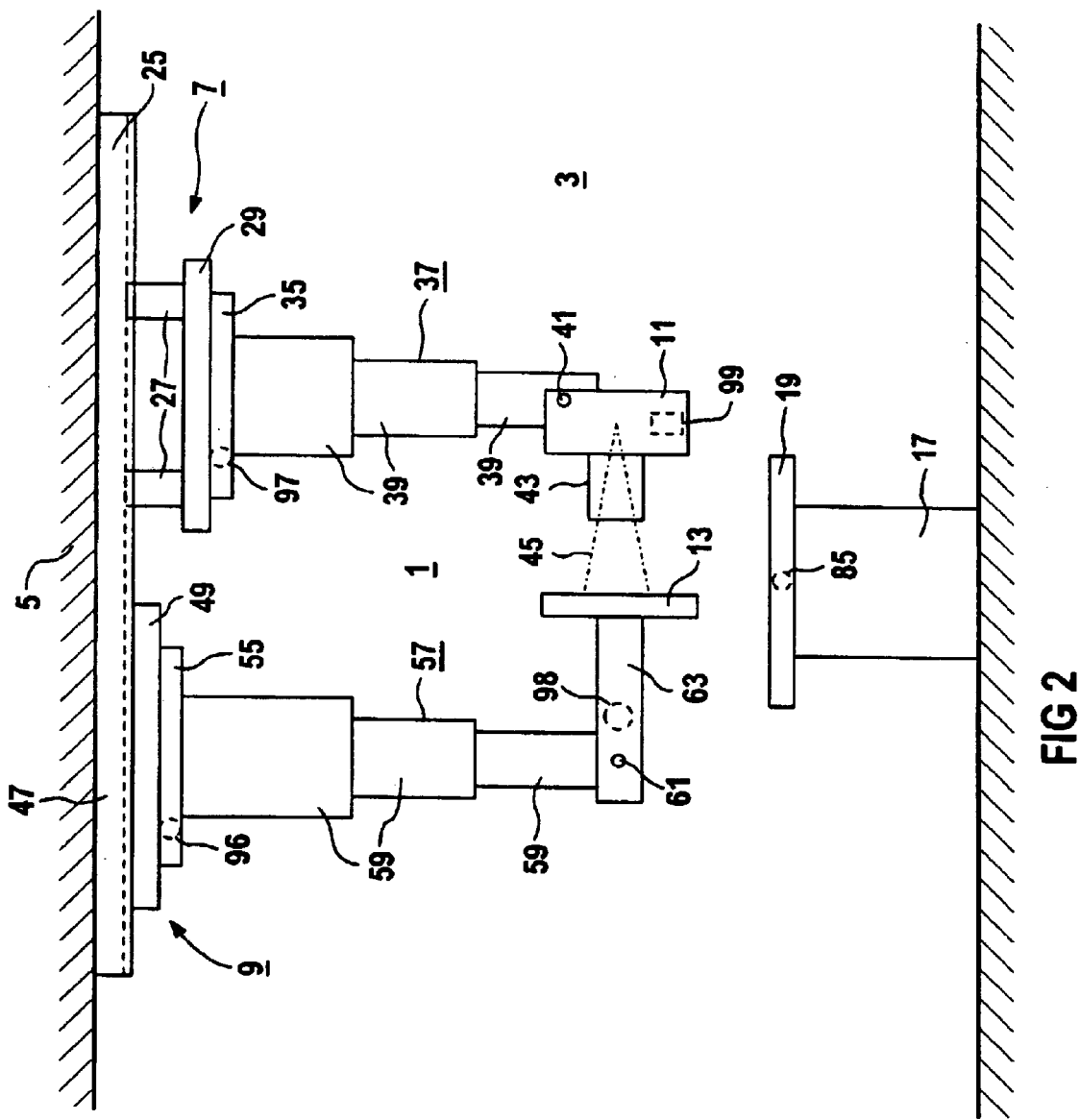
FIG. 2 shows the X-ray examination device of FIG. 1 in an end-face view.
Figure 3:
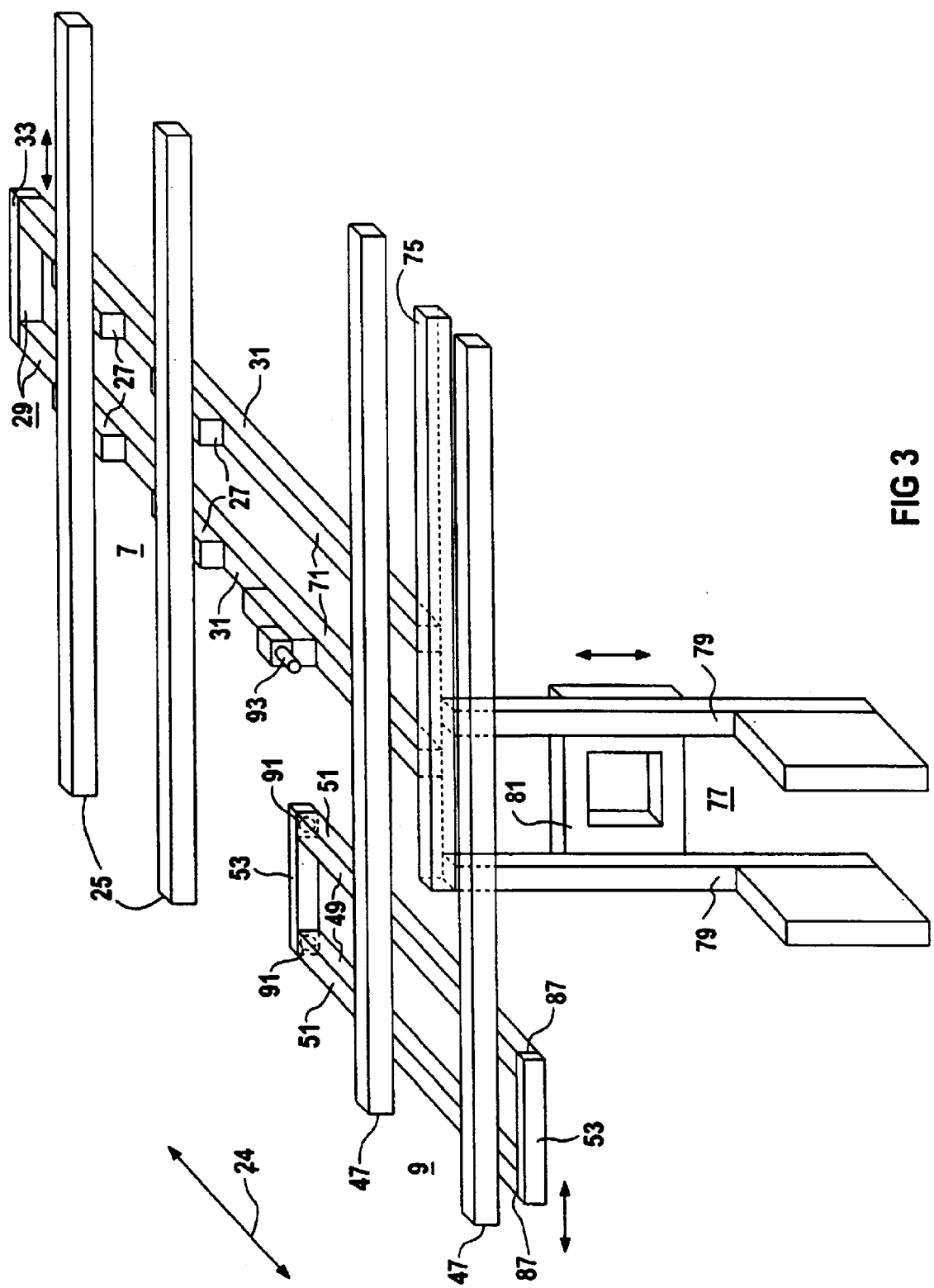
FIG. 3 shows adjustment devices of an X-ray examination device of the invention in a second exemplary embodiment, in perspective.

FIG. 2 also can be referenced for further explanation of the adjustment devices 7, 9, this showing the X-ray examination device 1 from a viewing direction 23. FIG. 3 also can be consulted for elucidation, this showing the adjustment devices 7, 9 in perspective as viewed from an elevated position. The patient orientation 24 is entered therein at the side.

The first adjustment device 7 has a first guide rail 25 fashioned as horizontal double rail that is oriented perpendicularly to the patient bed 19 and is secured to the ceiling 5. A horizontal, first transverse carrier 29 extending transversely relative to the first guide rail 25 is attached at the bottom to the first guide rail 25 via four blocks or spacers 27. The first transverse carrier 29 is secured to and guided at the first guide rail and can be horizontally moved or displaced along the latter. Roller or plain bearings can be provided for guidance. The first transverse carrier 29 is fashioned as a square frame (see FIG. 3) with two parallel longitudinal beams 31 and two cross beams 33 that terminate and connect the former. A first telescoping truck or first column truck 35 is movable or displaceable along the first transverse carrier 29 transversely to the first guide rail 25 and likewise horizontally. In a downward direction, the first column truck 35 carries a radiator stand 37 that has a downwardly extendable, three-part telescoping column 39. The X-radiator 11, with a diaphragm 43 attached thereto at the output side, is secured to the end side of the telescoping column 39 via an articulation 41 (see FIG. 2). The telescoping column 39 is drivable manually or—optionally—in motorized fashion. Under remote control, the X-ray radiator 11 is rotatable around a vertical axis and is pivotable around a horizontal axis. The X-ray radiator 11 emits X-rays 45 that can be detected by the radiation receiver 13.

In a way analogous to the first adjustment device 7, the second adjustment device 9 has a second guide rail 47 that is fashioned as a horizontal double rail and is secured to the ceiling 5. In the downward direction, a second transverse truck or second transverse carrier 47 extending transverse to the second guide rail 47 is movably attached to the second guide rail 47 and is likewise composed of two longitudinal beams 51 and two cross beams 53 to form a rectangle (see FIG. 3). A second telescoping truck or second column truck 55 is movable transverse to the second guide rail 47 in or at the second transverse carrier 49. A detector stand 57 is attached to the underside of the second column truck 55, the stand 57 having a downwardly extendable telescoping column 59 to which an arm 63 carrying the radiation receiver 13 is attached at the end side via an articulation 61. The radiation receiver 13 is rotatable around a vertical axis and pivotable around a horizontal axis, and thus can be optimally aligned to the X-radiator 11.

The spacers 27 are dimensioned such that—seen in the side view of FIG. 1—the two transverse carriers 29, 29 are arranged essentially above one another in the region of the projecting length LU of the first transverse carrier 29. The two transverse carriers 29, 49 are attached such at different heights that they can be moved past one another—above or below dependent on standpoint—when they are moved either manually or automatically in opposite direction along the guide rails 25, 47.

To this end, the second guide rail 47 together the second transverse carrier 49 attached to it is laterally arranged next to the first guide rail 25 and the spacers 27 (see FIG. 1). The first transverse carrier 29 is fashioned such that the majority part of its length LU projecting laterally beyond the appertaining guide rail 25 projects at only one side of the guide rail 25 as boom 71. This boom 71 lies under the second transverse carrier 49 and can pass under it. The length L1 of the first transverse carrier 29 in the example amounts to approximately 2.5 m through 3.0 m, and the length L2 of the second transverse carrier 49 amounts to approximately 2.0 m.

Figure 6:
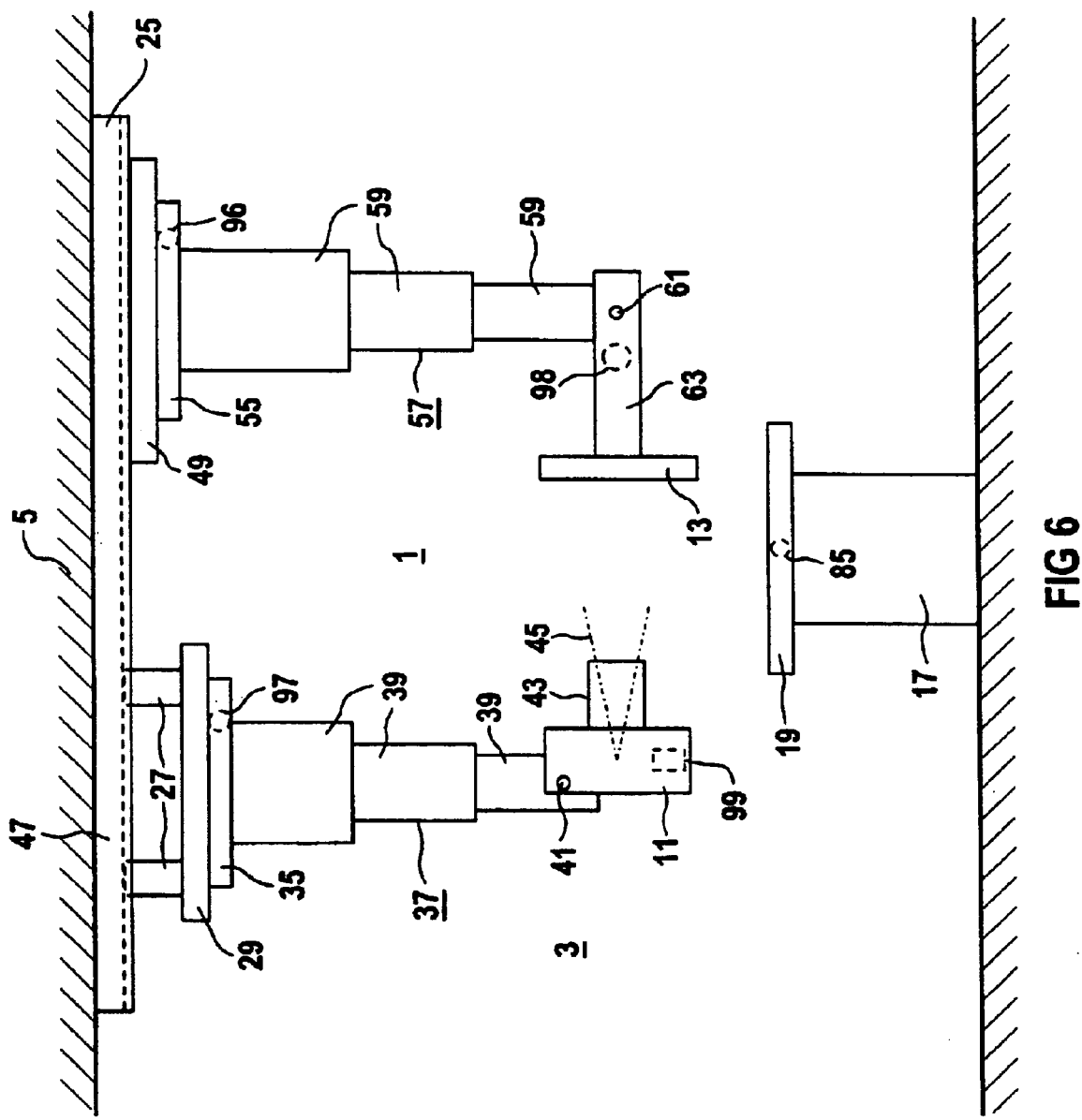
FIG. 6 shows the X-ray examination device of FIG. 5 in a front view.

A floor support 73 is present for increasing the mechanical stability of the boom 71, the upper end of said floor support 73 carrying a third guide rail 75. The third guide rail 75 (also see FIG. 3) proceeds under the second transverse carrier 49 and parallel to the other two guide rails 25, 47. The floor support 73 and the third guide rail 75 are omitted in FIGS. 2 and 6 for clarity and to allow a clear view from the viewing direction 23.

The adjustment devices 7, 9 of the X-ray examination device 1 of the invention are shown in greater detail in FIG. 3 in an oblique perspective view from above. For clarity, the ceiling 5, the column trucks 35, 55 as well as the bearing mechanism 15 and the patient 21 have been omitted from FIG. 3. The basic principle of the adjustment devices 7, 9 according to FIG. 3 is identical to that of the adjustment devices 7, 9 of FIGS. 1 and 2.

At the same time, FIG. 3 represents a second exemplary embodiment with the following, different features compared to FIGS. 1 and 2:

a) The floor support 73 of the X-ray examination device 1 according to FIG. 3 is integrated into a louver wall device 77 belonging to the X-ray examination device 1 in the exemplary embodiment of FIG. 3. The louver wall device 77 has two vertically attached columns 79 along which a frame 81 can be vertically moved, a solid-state detector, an X-ray film, a storage foil or a catapult louver drawer being capable of being installed therein.

b) The second guide rail in FIG. 1 is implemented comparatively broad compared to the first guide rail 25, i.e. its longitudinal beams have a greater distance from one another than the longitudinal beams of the first guide rail 25. This is advantageous for an especially stable bearing of the second transverse carrier 49. That this, however, is not compulsory derives from FIG. 3 wherein the two guide rails are shown of about the same width. It is advantageous, however, that the first guide rail 25 is so narrow that a large boom 71 that can pass under a large part of the second transverse carrier 49 is formed by the first transverse carrier 29.

Figure 4:
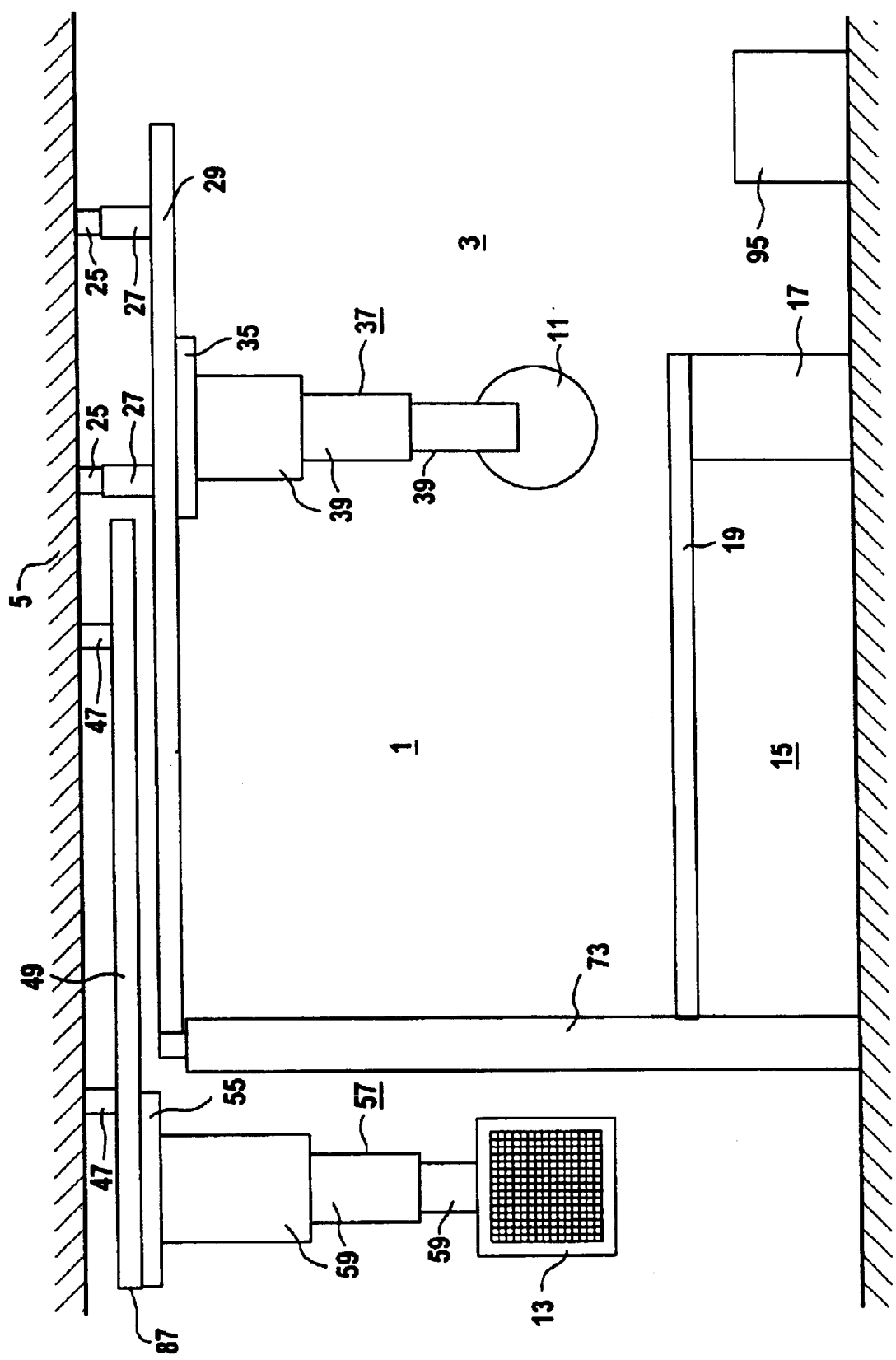
FIG. 4 shows the X-ray examination device of FIG. 1 with position of a radiation detector modified with respect thereto in a longitudinal side view.

Given the X-ray examination device 1 of the invention, it is possible—proceeding from the right operation shown in FIG. 2 (X-ray radiator at the right side of the support mechanism 15)—to change to a left operation, particularly program-controlled and/or automatically. Proceeding from FIG. 2, it is thereby possible to move both the X-ray radiator 11 as well as the radiation receiver 13 from their respective position shown in FIG. 2 onto the opposite side with respect to a middle longitudinal axis 85 of the bearing mechanism 15. As shown in FIG. 4, the second column truck 55 is moved to an end 87 of the second transverse carrier 49 at the side of the floor support or left side. In the side view of FIG. 4, the second transverse carrier 49 thus projects so far beyond the first transverse carrier 29 and beyond the floor support 73 that the radiation receiver 13 can travel past that side of the floor support 73 facing away from the first transverse carrier 29 (out of the plane of the drawing).

Figure 5:
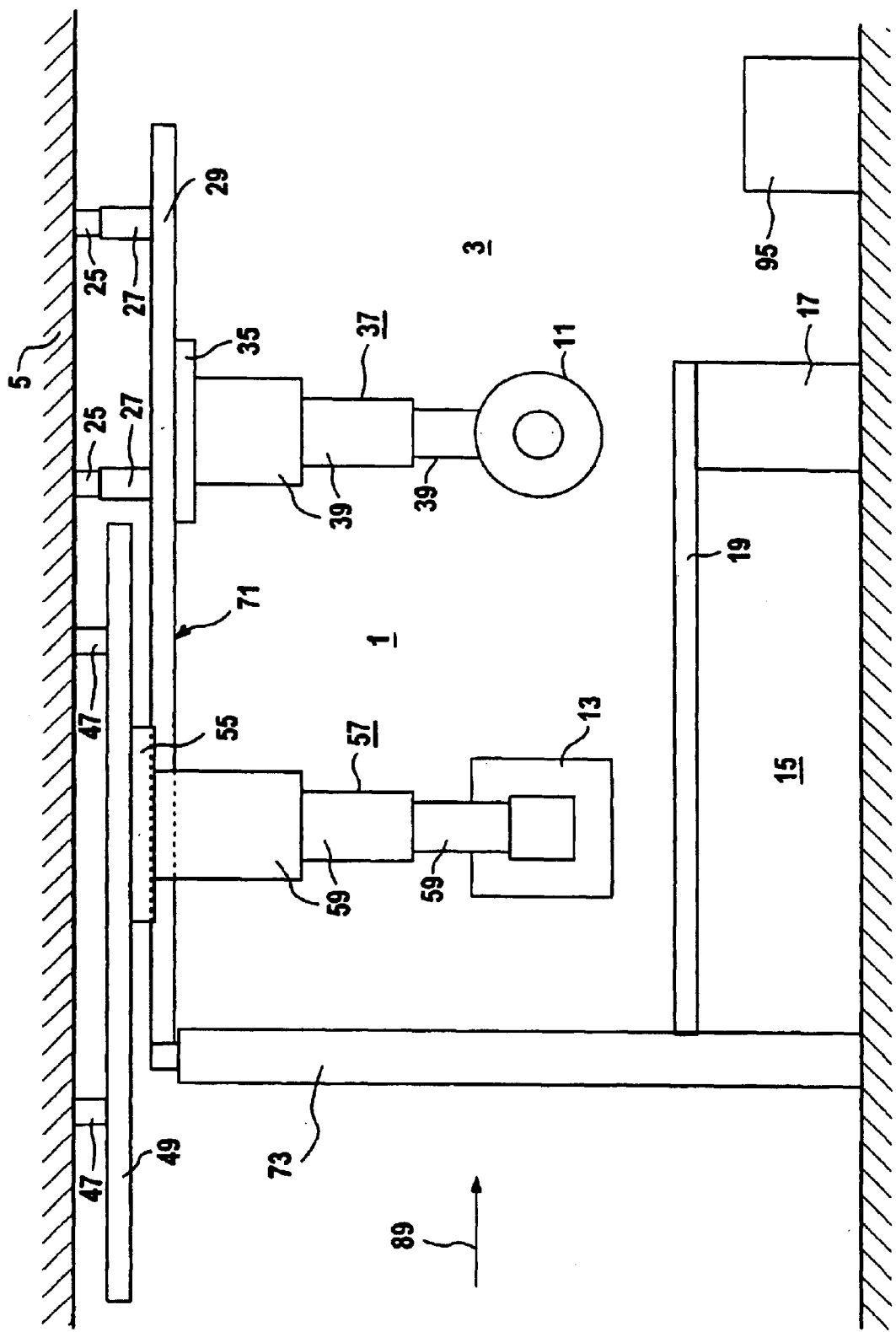
FIG. 5 shows the X-ray examination device of FIG. 4 with the position of the radiation detector modified, in a longitudinal side view.

FIG. 5 shows how the radiation receiver 13 with its detector stand 57 that has traveled past behind the floor support 23 in this way is now positioned in front of the first transverse carrier 29—in the viewing direction of FIG. 5. In the illustration of FIG. 5, the X-ray radiator 11 has been moved into the plane of the drawing with respect to the position shown in FIGS. 1 and 2, so that the X-ray radiator 11 and the radiation receiver 13—seen in the front view of FIG. 6—have changed sides with reference to the patient bed 19. Moreover, X-ray radiator 11 and the radiation receiver 13 have again been aligned relative to one another via the articulations 41, 61. The illustration of FIG. 6 derives when viewing the X-ray examination device 1 of FIG. 6 in the viewing direction 89.

The X-ray examination device 1 also has a control device 85 with which four or more drives 96, 97, 98, 99 (see FIG. 2) can be driven for the movement and/or orientation of the X-ray radiator 11 and/or radiation receiver 13. The drives 96, 97, 98, 99 are only schematically shown. The control device 95 enables a reconfiguring of the X-ray examination device 1 from right operation to left operation under program control. Moreover, a threading of the radiation receiver 13 into the louver wall device 77 can be selected at a control panel of the control device 95 or by a corresponding organ program.

The two transverse carriers 29, 49 are rigidly connectible to one another by a coupling device. In the example of FIG. 3, for example, bores 91 in the second transverse carrier 49 and a coupling pin 93 at the first transverse carrier are provided for this purpose. This is especially advantageous for purposes of angiography in order—proceeding from one side of the patient—to move the X-ray radiator 11 and the radiation receiver 13 in common.

Though not explicitly shown, devices for covered laying of cables for the drive of the X-ray radiator 11, for taking the reception signals of the radiation receiver 13 and for supplying control signals or electrical energy to the drives 96, 97, 98, 99 are present at both transverse carriers 29, 49.

The radiation receiver 13 is, for example, a flat detector, particularly an a:Si detector, for example a solid-state image converter as disclosed by German PS 43 21 789.

An X-ray generator (not shown) that is present for driving an X-ray tube of the X-radiator can be integrated in the first column truck 35. Especially short high-voltage cables and switching times can be used as a result.

Although modifications and changes may be suggested by those skilled in the art, it is the intention of the inventor to embody within the patent warranted hereon all changes and modifications as reasonably and properly come within the scope of his contribution to the art.

I claim as my invention:

1. An X-ray examination device for use in a room having a ceiling, comprising:

a support mechanism adapted to receive a patient to be examined, said support mechanism having a middle, longitudinal axis;

an X-ray radiator which emits X-rays;

a radiation receiver for detecting said X-rays;

a first adjustment device adapted for attachment to the ceiling for holding and moving said X-ray radiator;

a second adjustment device adapted for attachment to the ceiling for holding and moving said radiation receiver; and said first and second adjustment devices being cooperatively structured and operable to allow said X-ray radiator to be transferred from a first sides of said longitudinal axis to a second side, opposite said first side, of said longitudinal axis and said X-ray detector to be transferred from said second side to said first side of said longitudinal axis, and to allow said X-ray radiator to be transferred from said second side to said forst side of said longitudinal axis and said radiation receiver to be transferred from said first side to said second side of said longitudinal axis.

2. An X-ray examination device as claimed in claim 1 wherein said first adjustment device comprises a first guide rail disposed perpendicularly relatively to said longitudinal axis, and wherein said second adjustment device comprises a second guide rail disposed perpendicularly relative to said longitudinal axis.

3. An X-ray examination device as claimed in claim 2 wherein said first adjustment device comprises a first transverse carrier movably attached to said first guide rail, said X-ray radiator being mounted to said first transverse carrier so that said X-ray radiator is movable perpendicularly to said first guide rail, and wherein said second adjustment device comprises a second transverse carrier movably attached to said second guide rail, said radiation receiver being mounted to said second transverse carrier so as to be movable perpendicularly to said second guide rail.

4. An X-ray examination device as claimed in claim 3 wherein at least one of said first transverse carrier and said second transverse carrier has a length greater than 1.5 m.

5. An X-ray examination device as claimed in claim 3 wherein, as seen from a side of said first and second transverse carriers, at least a portion of one of said first and second transverse carriers is disposed above at least a portion of the other of said first and second transverse carriers.

6. An X-ray examination device as claimed in claim 3 wherein, as seen from a side of said first and second transverse carriers, one of said first and second transverse carriers projects beyond the other of said first and second transverse carriers.

7. An X-ray examination device as claimed in claim 3 wherein said first and second transverse carriers are disposed at respectively different heights relative to each other, so that one of said first and second transverse carriers, moving in a first direction, can be moved past the other of said first and second transverse carriers along said first and second guide rails, respectively.

8. An X-ray examination device as claimed in claim 3 wherein each of said first and second transverse carriers has a length and wherein at least one of said first and second transverse carriers has a majority of its length projecting laterally beyond the guide rail to which it is attached, forming a boom projecting at only one side of the guide rail to which said one of said first and second transverse carriers is attached.

9. An X-ray examination device as claimed in claim 8 further comprising a floor support supporting said boom at a side thereof facing away from the guide rail to which said one of said first and second transverse carriers is attached.

10. An X-ray examination device as claimed in claim 9 wherein said floor support carries a third guide rail for guiding said boom.

11. An X-ray examination device as claimed in claim 10 wherein said X-ray radiator and said X-ray receiver are supported components, and wherein the other of said first and second transverse carriers projects beyond said one of said first and second transverse carriers forming said boom, and beyond said floor support, so that the supported component carried by said other of said first and second transverse carriers can travel past said floor support at a side thereof facing away from said boom.

12. An X-ray examination device as claimed in claim 9 further comprising a louver wall device providing floor-side support for at least one of said first and second adjustment devices.

13. An X-ray examination device as claimed in claim 1 wherein said first adjustment device comprises a first plurality of drives for moving said X-ray radiator, and wherein said second adjustment device comprises a second plurality of drives for moving said radiation receiver, and wherein said X-ray examination device comprises a control device connected to said first plurality of drives and to said second plurality of drives for automatically causing each of said X-ray radiator and said radiation receiver to be selectively movable at each of said first and second sides of said longitudinal axis.

* * * * *